United States Patent [19]

Felix et al.

[11] Patent Number: 4,732,972

[45] Date of Patent: Mar. 22, 1988

[54] POLYPEPTIDES HAVING GROWTH HORMONE RELEASING ACTIVITY

[75] Inventors: Arthur M. Felix, West Caldwell; Edgar P. Heimer, Sparta, both of N.J.

[73] Assignee: Hoffmann-La Roche Inc., Nutley, N.J.

[21] Appl. No.: 789,922

[22] Filed: Oct. 21, 1985

Related U.S. Application Data

[63] Continuation of Ser. No. 577,660, Feb. 7, 1984, abandoned, which is a continuation-in-part of Ser. No. 472,700, Mar. 7, 1983, abandoned.

[51] Int. Cl.$^4$ ............................................ C07C 103/52
[52] U.S. Cl. ................................................... 530/324
[58] Field of Search ........................... 530/324; 514/12

[56] References Cited

U.S. PATENT DOCUMENTS

| | | |
|---|---|---|
| 4,528,190 | 7/1985 | Vale, Jr. et al. ....................... 514/12 |
| 4,529,595 | 7/1985 | Rivier et al. ........................... 514/12 |
| 4,562,175 | 12/1985 | Chang et al. .......................... 514/12 |
| 4,595,676 | 6/1986 | Spiess et al. .......................... 514/12 |
| 4,617,149 | 10/1986 | DiMarchi et al. ................... 530/324 |

FOREIGN PATENT DOCUMENTS 0117034 8/1984 European Pat. Off. .
0138416 4/1985 European Pat. Off. .

OTHER PUBLICATIONS

Ling, et al., Biochemical and Biophysical Research Communications, 123:854–861, 1984.
Rivier, et al., Letters to Nature, 300:276–278; 1982.
Guillemin, et al., Science, 218:585–587; 1982.
Hruby, V. J. and D. H. Rich, Editors, Peptides Structure and Function, pp. 853–856, Pierce Chemical Co., Rockford, Ill.
Unlisted Drugs, vol. 35, No. 3, Mar. 1983.

Primary Examiner—J. R. Brown
Assistant Examiner—F. T. Moezie
Attorney, Agent, or Firm—Jon S. Saxe; George M. Gould; Julie M. Prlina

[57] ABSTRACT

Polypeptides corresponding to growth hormone releasing factor in which methionine at position 27 has been replaced by a leucine residue retain full growth hormone releasing activity. In the case of the full length (44-amino acid) polypeptide, the leucine analog has full biological activity in the free acid form, unlike the natural growth releasing factor which requires carboxy terminal amidation for full biological activity.

3 Claims, No Drawings

POLYPEPTIDES HAVING GROWTH HORMONE RELEASING ACTIVITY

RELATED APPLICATIONS

This application is a Rule 1.62 Continuation of Ser. No. 577,660 filed Feb. 7, 1984 now abandoned which Ser. No. 577,660 was in turn a continuation-in-part of application Ser. No. 472,700, filed Mar. 7, 1983, now abandoned.

BACKGROUND OF THE INVENTION

Dr. Guillemin and coworkers at the Salk Institute have recently (*Science,* 218, 585–587 (Nov. 5, 1982), see also *New York Times,* Oct. 29, 1982 at page 1, column 2) reported the isolation, synthesis, and biological activity of a group of related substances they have called growth hormone releasing factor (GRF). This factor has been sought after for decades by scientists but such search has been, until now, unrewarding due to the minute quantities in which such substance occurs naturally.

The successful isolation of GRF has been due in part to the discovery of the ectopic production of GRF in large amounts by pancreatic tumors associated with acromegaly. Three forms of GRF derived from the pancreatic tumor have been observed. These forms, consisting of three homologous peptides of 44, 40 and 37 amino acids in length, are identical at the amino terminal and differ in the termination point of the carboxyl terminal. The 44-amino acid GRF is further distinguished in having an amide group at the carboxy terminus whereas the other two forms have a free carboxy group at that terminus. It has been found that removal of the amide group to produce the free acid form of the 44 amino acid GRF results in a significant loss of biological activity.

The amidated form of GRF(1-44) is apparently the parent molecule and has been indicated to possess the highest biological activity in vitro. However, all three peptides have been found to be virtually equally potent in vivo. It has further been shown that the removal of the amino terminal tyrosine from GRF results in complete loss of bioactivity indicating that the active core of the molecule starts with the first amino terminal amino acid.

Rivier and coworkers have recently reported (*Nature,* 300, 276–278, Nov. 18, 1982) that synthetically produced GRF(1-29)-$NH_2$, GRF(1-32)-$NH_2$, GRF(1-39)-$NH_2$ and GRF(1-40)-$NH_2$ displayed in vitro biological activity at similar potencies (with a factor of 2) to GRF(1-40)-OH.

Growth in animals is believed to be regulated by a cascade of bio-regulatory molecules. Thus, the hypothalmus produces GRF which in turn acts upon the pituitary to cause release of growth hormone. The pituitary is maintained under negative feedback control by somatostatin and insulin growth factor (IGF). GRF has been found to be enormously active, exhibiting an $ED_{50}$ of approximately 50 fmole/ml or 75 pg/ml and has been found to release micrograms/ml levels of growth hormone in the blood. Thus, GRF can be utilized therapeutically in most of the areas now considered candidates for treatment by growth hormone. Examples of such therapeutic uses include the treatment of pituitary dwarfism, diabetes resulting from abnormalities in growth hormone production, enhancement of wound healing, treatment of burns and retardation of the aging process. Due to its favorable potency compared to growth hormone itself, GRF will have major advantages in the agricultural field as well. Agricultural uses would include, for example, stimulating development of fowl or animals raised for meat so as to allow either marketing at an earlier time or else allow the farmer to produce a larger animal per equal time on feed to present methodology. In addition, GRF would be useful in stimulation of milk production in dairy cows and increasing egg production in chickens.

While GRF in its various forms is of a molecular size which would allow for synthesis by either solid phase or solution phase peptide synthetic methods, it is believed that for economic, large scale production of these therapeutically valuable substances the use of recombinant DNA technology is preferred. Using known techniques of DNA recombination, a DNA sequence containing the structural code for GRF could be inserted into a replicable expression vehicle under the control of appropriate control elements including a promoter-operator sequence and a sequence coding for a ribosome binding site. The expression vehicle would then be used to transform a host microorganism, such as a bacterium, which would be grown up and subjected to conditions under which it would express GRF.

Unfortunately, several potential problems exist which hinder the production of GRF by recombinant DNA technology. It has been observed that polypeptides having the molecular size of GRF tend to be more subject to degradation by the proteases which are present in bacteria such as *E. coli* than are larger protein molecules. Moreover, for reasons which are not fully understood, the cellular machinery which regulates transcription and translation apparently operates more efficiently with longer chain DNA, thus making it difficult to achieve acceptable levels of expression of smaller polypeptides such as GRF. Yet another problem which must be overcome if GRF is to be produced by recombinant DNA technology is that of finding a suitable means of purifying and isolating the GRF from the other bacterial proteins and endotoxins produced by bacterial hosts such as *E. coli.*

It has been suggested to ligate a DNA sequence encoding the amino acid sequence of GRF with a DNA sequence encoding the amino acid sequence of a larger protein whose amino acid sequence is known and inserting the ligated DNA sequence into an expression vector for the purpose of expressing a fused protein. The fused protein would be much less susceptible to degradation by bacterial proteases than would GRF alone. One could select a fusion protein which is known to be capable of expression at high levels in known expression vectors, for example an interferon protein, and thereby obtain high levels of expression of the fused GRF. Moreover, since there are available monoclonal antibodies which selectively recognize and bind antigenic sites on the interferon protein, one could conveniently purify the fused GRF-interferon protein by passing a crude bacterial extract containing the fusion protein through a column in which the monoclonal antibody is bound to a solid support and then eluting the bound fusion protein from the column using an appropriate elution solvent.

Once the fusion protein was purified, the GRF polypeptide would have to be cleaved from the fused interferon (or other fused protein) and isolated. Cyanogen bromide cleavage is the simplest method by which such cleavage could be effected. Since cyanogen bromide selectively cleaves at the carboxy side of a methionine residue, it would be necessary to construct the ligated DNA sequence by inserting a nucleotide codon for methionine immediately after the codon for the carboxy terminal amino acid residue of the interferon and before the codon for the first amino acid residue of GRF.

The aforementioned strategy for producing GRF by recombinant DNA technology suffers one flaw; to wit, the GRF polypeptide sequence identified by Dr. Guillemin contains a single methionine residue at position 27. Thus, cyanogen bromide cleavage to liberate the GRF from the expressed fusion protein could not be effected without simultaneously cleaving the GRF polypeptide itself. Another, albeit less serious, drawback is that the carboxy-terminus of the GRF produced by recombinant DNA technology would be in the form of an acid, rather than an amide. In the case of the full sequence polypeptide, GRF(1-44), this would mean that an additional and costly amidation step would be necessary to obtain the polypeptide in its fully active form.

SUMMARY OF THE INVENTION

This invention is based on the discovery that the methionine residue at position 27 of the GRF molecule can be replaced by a different appropriately selected amino acid residue without loss of growth hormone releasing activity. In particular, we have found that a polypeptide having an amino acid sequence corresponding to GRF in which the methionine residue at position 27 has been replaced by a leucine residue has full biological activity. Further, and quite surprisingly, we have found that the carboxy-terminus free acid form of the 44-amino acid GRF analog in which methionine has been replaced with leucine at position 27 has biological activity which is equal to or greater than that of natural carboxy-terminus amidated GRF-(1-44). Similar results have been found with the norleucine analog at position 27.

Thus, there is provided in accordance with the teachings of the present invention a polypeptide having growth hormone releasing activity which can be produced by the recombinant DNA technique outlined above without fear that the active polypeptide will be internally cleaved by cyanogen bromide and without the need to perform a final amidation step to restore full biological activity.

The analogs of this invention have a further advantage over natural GRF inasmuch as the leucine residue is not subject to oxidation, as is the methionine residue of natural GRF, which may be oxidized to methionine sulfoxide. Therefore, the polypeptide of this invention is believed to be more stable than natural GRF.

DETAILED DESCRIPTION OF THE INVENTION

As used herein, the term "GRF" refers to human growth hormone releasing factor, which is a polypeptide having the amino acid sequence (*Science*, 218, 585, Nov. 5, 1982)

```
   1              5                  10
Tyr—Ala—Asp—Ala—Ile—Phe—Thr—Asn—Ser—Tyr—

15                  20
—Arg—Lys—Val—Leu—Gly—Gln—Leu—Ser—Ala—Arg—

25                  30
—Lys—Leu—Leu—Gln—Asp—Ile—Met—Ser—Arg—Gln—

35                  40
—Gln—Gly—Glu—Ser—Asn—Gln—Glu—Arg—Gly—Ala—

—Arg—Ala—Arg—Leu
``` or biologically active fragments having at least the first 28 amino acids of the full polypeptide and displaying growth hormone releasing activity. The suffixes "-OH" and "-NH$_2$" following "GRF" refer to the free acid and amide forms of the polypeptide, respectively. In the event neither suffix is used, the expression is intended to encompass both forms. Analogs of GRF are indicated by setting forth the substituted amino acid in parentheses before "GRF"; that is, for example, "(Leu$^{27}$)-GRF" indicates a polypeptide having an amino acid sequence corresponding to GRF in which a leucine residue has been substituted for methionine at position 27. Numbers in parentheses following "GRF" indicate fragments of the full polypeptide by giving the position numbers of the amino acid residues, e.g. GRF(1-40) indicates a fragment having the first 40 amino acids of the full sequence.

As previously indicated, the invention is directed to polypeptides corresponding in amino acid sequence to GRF in which the methionine residue at position 27 has been substituted by a different amino acid which has been selected to prevent the polypeptide from being cleaved by cyanogen bromide while allowing the polypeptide to retain growth hormone releasing activity. Suitable substituent amino acids are those which are structurally similar to methionine but which are not recognized and cleaved by cyanogen bromide, i.e. leucine, isoleucine, norleucine and valine. We prefer to employ leucine as the substituent which we have found results in a full length polypeptide having full growth hormone releasing activity in the free acid form.

The polypeptides of this invention can be prepared by recombinant DNA technology, as previously outlined, or they can be prepared by solid phase peptide synthesis techniques or by solution phase peptide synthesis. We prepared (Leu$^{27}$)-GRF(1-44)-OH by the solid phase peptide synthesis procedure using aminoacyl-4-(oxymethyl)-phenylacetamidomethyl (PAM) resin as a solid support. The polypeptide was purified by preparative high pressure liquid chromatography (HPLC) and was shown to be homogeneous by two analytical HPLC systems, isoelectric focusing and high voltage thin layer electrophoresis and gave the expected amino acid composition. The corresponding amide, (Leu$^{27}$)-GRF-(1-44)-NH$_2$, can be produced by using benzhydrylamine resin as the solid support for solid phase peptide synthesis. Those skilled in the art will recognize that when PAM resin is used, treatment with HF to remove the polypeptide from the solid support results in a polypeptide having a terminal carboxyl group whereas treatment with HF to remove the polypeptide from benzhydrylamine resin results in a polypeptide having a terminal amide group. Since norleucine is not a natural amino acid and thus cannot be introduced by recombinant technology, compounds of the invention with the norleucine substitution of position 27 are prepared by conventional peptide synthesis.

Purification of the polypeptide can be effected using procedures well known in peptide chemistry. As previously indicated, we purified the polypeptide obtained from the solid phase synthesis using preparative HPLC;

however, other known chromatographic procedures such as gel permeation, ion exchange and partition chromatography can also be employed.

The polypeptides of this invention have growth hormone releasing activity. Accordingly, they are useful in the treatment of growth-related disorders such as pituitary dwarfism and diabetes resulting from abnormalities in growth hormone production. They can also be used to stimulate the growth of animals raised for meat production.

Appropriate dosages of the polypeptides of the invention to be administered will vary somewhat depending on the individual subject and the conditon being treated. The skilled worker will be able to determine appropriate dosages based on the known circulating levels of growth hormone associated with normal growth and the growth hormone releasing activity of the polypeptide. Since applicants' $(Leu^{27})$-GRF-OH has been shown to release growth hormone in vitro at levels on the order of ten times or more the amount of $(Leu^{27})$-GRF-OH administered, it is quite apparent that considerably lower dosages can effectively be employed than if one administered growth hormone directly for the same purpose. The dosage to be administered for the treatment of growth-related disorders will also vary somewhat from individual to individual depending upon the degree of insufficiency of growth hormone production. Generally, a dosage of about 0.5 μg/kg., based on body weight of the subject, is sufficient to stimulate the desired release of growth hormone. The dosages employed to stimulate supernormal growth activity in livestock will be significantly higher (per kg. of subject weight) than the dosages employed to restore normal growth in cases of growth hormone deficiencies such as pituitary dwarfism in humans.

Thus, there is provided in accordance with this invention a method of treating growth-related disorders characterized by insufficient production of growth hormone which comprises administering an amount of $(Leu^{27})$-GRF sufficient to stimulate the production of growth hormone at levels associated with normal growth.

Normal levels of growth hormone vary considerably among individuals and, for any given individual, levels of circulating growth hormone vary considerably during the course of a day. In adult humans, normal serum levels of growth hormone have been reported to vary from about 0–10 nanograms/ml. In children, normal serum levels of growth hormone have been reported to vary from about 0–20 nanograms/ml.

In order to effectively treat pituitary dwarfism with $(Leu^{27})$-GRF, treatment is administered during the period of normal growth. In females, this period generally does not extend far beyond the onset of menses. Thus, treatment of females should be effected prior to an age of from about 12 to 16 years, depending upon the individual. In males, the stimulation of growth may be possible for a considerably longer period of time beyond puberty. Thus, effective treatment of males will normally be possible up to about 18 to 19 years of age and, in some individual cases, up to about 25 years.

There is also provided a method of increasing the growth rate of animals by administering an amount of $(Leu^{27})$-GRF sufficient to stimulate the production of growth hormone at a level greater than that associated with normal growth.

The polypeptides of the invention can be administered in the form of human or veterinary pharmaceutical compositions which can be prepared by conventional pharmaceutical formulation techniques. Compositions suitable for intravenous, subcutaneous, intramuscular or intraperitoneal administration may be employed. A suitable dosage form for pharmaceutical use is from about 0.01 to about 0.5 mg of $(Leu^{27})$-GRF-OH, which may be lyophilized for reconstitution with sterile water or saline. The composition should be maintained at a pH below about 6.0 in order to maintain the stability of the $(Leu^{27})$-GRF-OH. Serum albumin from the species being treated (e.g. human serum albumin in the case of humans, bovine serum albumin in the case of cows and so forth) may also be present together with other known pharmaceutical adjuvants.

The following examples are presented in order to illustrate the practice of this invention and are not to be construed as limiting the scope of the invention in any way. Unless otherwise stated, all parts and percents are given by weight and all temperatures are in degrees centigrade.

In the examples, optically active protected amino acids in the L configuration were employed. The protected amino acids were examined by thin layer chromatography on silica gel G plates and developed with chlorine-TDM. Melting points were determined on a Thomas-Hoover apparatus (uncorrected) and optical rotation was measured in a jacketed 1-dm cell on a Perkin-Elmer Model 141 Polarimeter and conformed to the accepted values. Amino acid analysis was performed on a fluorescamine amino acid analyzer.

The following abbreviations are used in the examples to indicate various protecting groups.

BOC=t-butyloxycarbonyl
Z=benzyloxycarbonyl
2ClZ=2-chlorobenzyloxycarbonyl
Bzl=benzyl
2,6-Cl$_2$-Bzl=2,6-dichlorobenzyl
Tos=p-toluenesulfonyl

EXAMPLE 1

Preparation of $(Leu^{27})$-GRF-OH $(Leu^{27})$-GRF-OH was prepared by sequential coupling of amino acids using a commercially available automated solid phase peptide synthesizer. Nα-Boc-amino acids were used in the synthesis. Trifunctional amino acids were protected as Nα-Boc-Lys(2ClZ), Nα-Boc-Asp(OBzl), Nα-Boc-Glu(OBzl), Nα-Boc-Ser(Bzl), Nα-Boc-Thr(Bzl), Nα-Boc-Tyr(2,6-Cl$_2$-Bzl).

Boc-Leu-4-(oxymethyl)-phenylacetamidomethyl resin was prepared by coupling Boc-Leu-4-(oxymethyl)-phenylacetic acid to aminomethyl resin (10 g., 0.714 mmol./g.) as described in *J. Org. Chem.*, 43, 2845–2852 (1978). Amino acid analysis of the dried resin hydrolysate indicated a substitution of 0.135 mmol./g of polystyrene. The Leu-coupled resin was then placed in the reaction vessel of the automated synthesizer where the remaining amino acids of $(Leu^{27})$-GRF-OH were each sequentially coupled to the resin-bound amino acid chain by deprotecting the N-terminus of the chain and reacting the next amino acid in the sequence under conditions which promoted the formation of a peptide linkage at the N-terminus of the growing chain. A fourfold excess of each Boc-amino acid and dicyclohexylcarbodiimide (DCC) were used in each coupling and deprotection of the Boc-group was achieved by treatment with 50% trifluoroacetic acid (TFA) in methylene chloride.

Thus, 10 g. of Boc-Leu-4-(oxymethyl)-phenylacetamidomethyl resin was added to the reaction vessel and the following protocol was employed to couple each successive amino acid.

(1) Treat with 50% TFA in methylene chloride for 1 min.;
(2) Treat with fresh 50% TFA in methylene chloride for 20 min.;
(3) Wash with methylene chloride four times for 1 min.
(4) Wash with 8% diisopropylethylamine (DIEA) in methylene chloride for 2 min.;
(5) Wash with methylene chloride for 1 min.;
(6) Repeat steps 4 and 5;
(7) Wash with 2-propanol twice for 1 min.;
(8) Wash with methylene chloride six times for 1 min.;
(9) React four equivalents of Boc-amino acid in methylene chloride (50 ml./g.) for 5 min., followed by four equivalents of DCC for 20 min.;
(10) Treat with 1% DIEA in methylene chloride for 10 min.;
(11) Wash with methylene chloride for 2 min.;
(12) Repeat steps 10 and 11;
(13) Wash with methylene chloride six times for 2 min.

Exceptions to this protocol were that Boc-Gln was coupled as the preformed symmetrical anhydride (6 equivalents in dimethylformamide (DMF)) followed by a rapid wash and neutralization after removal of the Boc-group to minimize the formation of pyrrolidone carboxylic acid (Pca), the deprotected Gln residues were coupled with preformed symmetrical anhydride in DMF to further minimize Pca formation and Boc ASn-OH (6 equiv. in DMF) was coupled for 1 hr. by the DCC-1-hydroxybenzotriazole method (*Chem. Ber,* 103, 788–798 (1970) and *Int. J. Peptide Protein Res.,* 7, 495–501 (1975) to reduce nitrile formation. After the coupling of Ser(Bzl) at position 28, one gram of the peptide-resin (estimated to be approximately 100 μmol) was used for the synthesis of (Leu$^{27}$)-GRF-OH and the remainder removed for the preparation of other GRF analogs in which Leu$^{27}$ is replaced by other amino acid residues.

Coupling efficiency was monitored after every cycle by the ninhydrin method (*Analytical Biochem,* 34, 595–598 (1970)) and was generally judged to be complete after two couplings. Noted exceptions which required multiple couplings were as follows: (1) Boc Arg (Tos) in 10% DMF-CH$_2$Cl$_2$ to Ala$^{42}$, Gly$^{39}$ and Lys$^{12}$; (2) Boc-Lys (2-ClZ) to Val$^{13}$; (3) Boc-Asp (OBzl) to Ile$^{26}$; (4) Boc-Leu to Leu$^{23}$ and (5) Boc-Ser (Bzl) to Arg$^{29}$. The Boc group of the last amino acid residue was removed by the procedure described in *J. Am. Chem. Soc.,* 98, 2324–2328 (1976) and the peptide-resin dried. The resultant side-chain protected peptide-resin (corresponding to approx. 80 μmol) was treated with anhydrous liquid HF to deprotect the side chains and release the peptide from the resin. The peptide-resin was treated with a mixture of p-cresol (10%), dimethylsulfide (65%) and HF (25%) at 0° for 1 hr. followed by treatment with p-cresol (10%) and HF (90%) at 0° for 2 hr. After work up, 332 mg of crude (Leu$^{27}$)-GRF-OH was obtained. A portion of this material (50 mg) was purified by a semi-preparative HPLC system using a Whatman Partisil M-9 ODS-3 column (0.94×50 cm). The column was eluted with 0.5% TFA-H$_2$O/CH$_3$CN in a linear gradient mode going from 30–45% of CH$_3$CN in 2 hr. with a flow rate of 3 ml/min. Fractions (3 ml.) were collected and aliquots analyzed by analytical HPLC. The product emerged at 56–58 min. and the fractions were combined, evaporated and lyophilized. The remainder of the crude material was purified in the same manner and a total of 16.8 mg of product was obtained. Side-band fractions were pooled, evaporated, lyophilized and rechromatographed to give a total of 18.5 mg of pure material (5%). The purified product was shown to be homogeneous in two analytical HPLC systems, migrated to the cathode in the isoelectric focusing analysis and was homogeneous by high voltage thin layer electrophoresis $R_{Arg}=0.18$. Peptide mapping of a tryptic digest gave the expected six major fragments comprising residues (1–11), (13–20), (22–29), (30–38), (39–41) and 42–43). Additional fragments may result from partial tryptic cleavage. Amino acid analysis: Asp, 3.80; Thr, 0.83; Ser, 3.75; Glu, 7.27; Gly, 3.31; Ala, 4.68; Val, 1.02; Ile, 1.88; Leu, 6.25; Tyr, 1.77; Phe, 0.86; Lys, 2.07; Arg, 6.51.

Leu$^{27}$ analogs of biologically active fragments of GRF, e.g. (Leu$^{27}$)-GRF(1-40), (Leu$^{27}$)-GRF(1-39), (Leu$^{27}$)-GRF(1-32) or (Leu$^{27}$)-GRF(1-29), can be prepared in an analogous manner by simply coupling the resin to the last desired amino acid and programming the solid phase peptide synthesizer to begin the sequential couplings with the next-to-last amino acid and work back toward the N-terminus. For example, if one wishes to produce (Leu$^{27}$)-GRF(1-32), the resin would be coupled to glycine, the first amino acid coupled by the synthesizer would be glutamine, the second amino acid coupled would be glutamine, and so forth.

EXAMPLE 2

The biological activity of (Leu$^{27}$)-GRF(1-44)-OH was compared with that of natural GRF(1-44)-NH$_2$ which was isolated from a human pancreatic tumor of an individual suffering from acromegaly (Salk Institute standard hp-GRF-NH$_2$(NL-A-10)). The assay for biological activity, which is based on the ability to stimulate production of growth hormone in rat pituitary cells in tissue culture, was performed in the following manner.

Pituitaries from 30–40 male Sprague-Dawley rats (175 g) were removed aseptically after decapitation. The anterior lobes were collected, washed 3 times in sterile Hepes buffer (0.025M) (pH 7.35) and dispersed at 37° C. in 20–30-ml Hepes buffer (pH 7.35) containing collagenase (4 mg per ml) and Dispase (Protease grade II, 2 mg per ml). After gentle 100–110-min vortexing and trituration by Pasteur pipette, the dispersed cells were separated by centrifugation (150×g, 4 min) and re-suspended in Hepes buffer containing neuraminidase (8 μg/ml), and 200 μg/ml ethylenedinitrilotetraacetic acid (EDTA) disodium salt pH 7.35, for 10 min. The cells were washed twice with plating medium and plated on multiwell-plates (1.5×10$^5$ cells per ml) using the following defined medium: F-12/DMEM/(6:3:1) (Gibco: 430-1700/430-1600/320-2591) with 2 g BSA/l., 2.38 g Hepes/l, 50 mg Garamycin/l (Schering Co.). The medium in each well was supplemented either with (Leu$^{27}$)-GRF(1-44)-OH or natural GRF(1-44)-NH$_2$ at concentrations ranging from 3.1 to 200 fmol. per ml. of medium. Control wells contained no supplement. Plating was done with this medium added with 2% fetal calf serum to ensure rapid fixation of the cells. On the fourth day the cells were washed twice with the defined medium without fetal calf serum. Finally 900 μl of defined medium was added to each well plus 100 μl of the same medium containing each individual treatment, in triplicate. After 3 hours of incubation the medium was collected and diluted as required to conduct radioimmunoassays (RIAs) for rat growth hormone. RIAs were conducted using Sinha's anti-murine GH immune serum.

The results of the assays for natural GRF(1-44)-NH$_2$ are given in Table 1 and for (Leu$^{27}$)-GRF(1-44)-OH in Table 2.

TABLE 1

Growth Hormone Releasing Activity of GRF(1-44)-NH$_2$

| Dose f mol./ml. | Growth Hormone Released ng./ml. | Percentage of Control |
|---|---|---|
| Control | 82 | — |
| 3.1 | 117 | 143 |
| 6.3 | 158 | 193 |
| 12.5 | 210 | 256 |
| 25.0 | 261 | 318 |
| 50.0 | 343 | 418 |
| 100.0 | 433 | 528 |
| 200.0 | 522 | 637 |

TABLE 2

Growth Hormone Releasing Activity of (Leu$^{27}$)-GRF(1-44)-OH

| Dose f mol./ml. | Growth Hormone Released ng./ml. | Percentage of Control |
|---|---|---|
| Control | 82 | — |
| 3.1 | 133 | 162 |
| 6.3 | 167 | 204 |
| 12.5 | 223 | 272 |
| 25.0 | 270 | 329 |
| 50.0 | 342 | 417 |
| 100.0 | 423 | 516 |
| 200.0 | 532 | 649 |

It can be seen from the data presented in the tables that (Leu$^{27}$)-GRF(1-44)-OH exhibited growth hormone releasing activity at about the same level as GRF(1-44)-NH$_2$ or slightly higher. Relative potency of (Leu$^{27}$)-GRF(1-44)-OH compared to the Salk Institute standard was determined by computerized analysis of the above data to be 1.063.

EXAMPLE 3

Synthesis of Nle$^{27}$-GRF(1-44)-NH$_2$ and Leu$^{27}$-GRF(1-44)-NH$_2$

Methods

Peptide assemblage was performed on the Vega Model 296 Peptide Synthesizer. Trifunctional amino acids were protected as: N$^\alpha$-Boc-Lys (2-ClZ), N$^\alpha$-Boc-Asp (OBzl), N$^\alpha$-Boc-Glu (OBzl), N$^\alpha$-Boc-Ser (Bzl), N$^\alpha$-Boc-Thr (Bzl), N$^\alpha$-Boc-Tyr (2,6-Cl$_2$-Bzl) and N$^\alpha$-Boc-Arg (Tos).

Boc-Leu-benzhydrylamine resin was prepared by coupling Boc-Leu to benzhydrylamine-resin (25 g, 0.5 mmol/g). Amino acid analysis of the dried resin hydrolysate indicated a substitution of 0.3 mmol/g. The remaining unreacted amino groups were acetylated by treating the resin with acetic anhydride-pyridine (1:1 v/v).

Peptide synthesis was carried out in a stepwise fashion. Double couplings were done by the preformed symmetrical anhydride procedure. All solvents were used in a ratio of 15–20 ml/g. The protocol for a typical cycle was as follows:
(1) 50% CF$_3$COOH—CH$_2$Cl$_2$ for 1 min, (2) 50% CF$_3$COOH—CH$_2$Cl$_2$ for 30 min, (3) CH$_2$Cl$_2$ 4 times for 1 min, (4) 8% DIEA-CH$_2$Cl$_2$ for 2 min, (5) CH$_2$Cl$_2$ for 1 min, (6) repeat steps 4 and 5, (7) 2-propanol twice for 1 min, (8) CH$_2$Cl$_2$ 6 times for 1 min, (9) 6 equivalents preformed symmetric anhydride of Boc-amino acids for 20 min, (10) 1% DIEA-CH$_2$Cl$_2$ for 10 min, (11) CH$_2$Cl$_2$ once for 2 min, (12) repeat steps 9, 10 and (12) CH$_2$Cl$_2$ 6 times for 2 min. Exceptions to this protocol were: (1) the couplings of Boc-Gln as the preformed symmetrical anhydride (6 eq; DMF) followed by a rapid wash and neutralization after removal of the Boc-group to minimize the formation of pyrrolidone carboxylic acid (Pca), (2) Couplings to the deprotected Gln residues were carried out with preformed symmetrical anhydrides in DMF to further minimize Pca formation, (3) Boc-Asn-OH (6 equiv. in DMF) was coupled for 1 h by the DCC-1-hydroxybenzotriazole method to reduce nitrile formation.

Coupling efficiency was monitored, after every cycle, by the ninhydrin method and was generally judged to be complete after 2 or 3 couplings. Whenever the Kaiser test was still positive, even after multiple couplings, coupling of the unreacted NH$_2$-terminal residues was done with AC$_2$O-pyridine.

EXPERIMENTAL

Synthesis of Boc-Leu-BHA-resin, 1

Boc-Leu-BHA-resin, 1, was prepared by coupling Boc-Leu-OH (11.55 g, 50 mmol) in CH$_2$Cl$_2$ (150 ml) to benzhydrylamine resin (25 g, 0.5 mmol) with DCC (10.31 g, 50 mmol) for 20 h. The Boc-Leu-BHA-resin (1) was washed with CH$_2$Cl$_2$ (3×400 ml), MeOH (3×400 ml), CH$_2$Cl$_2$ and dried. Substitution: 0.30 mm/g. The remaining unreacted amino groups were terminated with Ac$_2$O-pyridine.

Synthesis of Boc-GRF(28-44)-BHA-resin, 2

Boc-Leu-BHA-resin (1, 25 g, 7.5 mmol) was charged into the reaction vessel of the Vega 296 Peptide Synthesizer and solid phase synthesis performed as outlined in the methods section. After the coupling of Boc-Ser (Bzl)-OH to Arg (position 29) the peptide resin was dried to give 46.69 g of Boc-GRF(28-44)-BHA-resin.

Synthesis of Leu$^{27}$-GRF(1-44)-NH$_2$

A portion of 2 (2.5 g, 0.4 mmol) was charged into the reaction vessel of the Vega 296 Synthesizer and solid phase synthesis carried out by coupling with Boc-Leucine followed by the remaining 26 cycles in the GRF sequence as outlined in the methods section to give 2.78 g of peptide-resin. A 1.88 g portion was cleaved in 2 HF reactions using p-cresol (10%); dimethylsulfide (65%).HF (25%) [total volume: 10 ml] at 0° for 1 h, evaporated and followed by and cleavage with p-cresol (10%).HF (90%) [total volume: 10 ml] at 0° for 2 h. The HF was evaporated at 0° and the crude product triturated with ethyl acetate, extracted into TFA, evaporated and the residue triturated with ether and dried. A total of 1.0064 g of crude product was obtained.

A portion (8.75 mg) was purified by preparative hplc in an ODS-3 (C$_{18}$) M-20 (Whatman) (2×50 cm) column by dissolving in H$_2$O (10 ml), filtration, and elution with H$_2$O (0.5% TFA)-acetonitrile (0.25% TFA); Gradient: 10–32% (120 min.), 32% (50 min.) and 32–38% (90 min.); flow rate: 6 ml/min. Fractions 131–135 gave a total of 50 mg of semi-pure product which was further purified in an ES Industries (C$_8$) (1.5×30 cm column). Eluent: H$_2$O (0.5% TFA)-acetonitrile (0.25% TFA); Gradient: 30–60% (150 min); Flow rate: 4 ml/min. Fractions 49–51 gave a total of 26 mg of pure product (1.5% yield). Additional product could be obtained from the side-bands. Amino acid anal: Asp, 4.24; Thr 1.08; Ser, 3.94; Glu, 6.92; Gly, 2.98; Ala, 4.78; Val, 0.97; Ile, 1.97; Leu, 5.97; Tyr, 2.01; Phe, 0.99; Lys, 1.92; Arg, 6.12.

Synthesis of $Nle^{27}$-GRF(1-44)-$NH_2$

Another portion of 2 (2.5 g) was reacted in the same way as outlined for the preparation of $Leu^{27}$-GRF(1-44)-$NH_2$ except that Boc-Nle-OH was coupled followed by the remaining Boc-amino acids comprising the GRF sequences as outlined in the methods section to give 2.78 g of peptide-resin. A 2.03 g portion was cleaved in two HF reactions exactly as outlined above for $Leu^{27}$-GRF(1-44)-$NH_2$ to give a total of 1.0721 g of crude product.

Purification was carried out by preparative hplc on an ODS-3 ($C_{18}$) $M_{20}$ (Whatman) #6P1134 (2×50 cm) column by dissolving the crude product in $H_2O$ (10 ml), filtration through 0.45A type HA filter and eluted in the above column. Eluant: $H_2O$ (0.5% TFA)-acetonitrile (0.25% TFA); Gradient: 10-32% (120 min.); Flow rate: 6 ml/min. Fractions 153-165 gave a total of 121.7 mg of semi-pure product which was further purified by preparative hplc on an ES Industries ($C_8$)(2×30 cm column). Eluant: $H_2O$ (0.5% TFA)-acetonitrile (0.25% TFA); Gradient: 10-32% (120 min.); Flow rate: 4 ml/min. Fractions 50-55 gave a total of 60.7 mg of pure product (4.14% yield). Amino acid anal: Asp, 4.26; Thr, 0.75; Ser, 2.27; Glu, 7.13; Gly, 2.92; Ala, 4.67; Val, 1.00; Ile, 1.90; Leu, 5.12; Nle, 1.09; Tyr, 1.94; Phe, 0.91; Lys, 1.96; Arg, 6.07.

Bioassay of $[Leu^{27}]$-GRF(1-44)-$NH_2$ and $[NLeu^{27}]$-GRF(1-44)-$NH_2$ in the rat cell culture test described in Example 2 indicated average relative potencies of 0.42 and 0.89 respectively for these compounds when compared to the Salk Institute standard. Neither of these values was significantly different from the standard.

We claim:
1. $(Leu^{27})$-GRF(1-44).
2. $(Leu^{27})$-GRF(1-44)-OH.
3. $(Leu^{27})$-GRF(1-44)-$NH_2$.